United States Patent
Kammerer et al.

(10) Patent No.: US 10,584,123 B2
(45) Date of Patent: Mar. 10, 2020

(54) PHARMACEUTICAL FORMS OF DIAZABICYCLOOCTANE DERIVATIVES AND MANUFACTURING METHOD THEREOF

(71) Applicants: Fedora Pharmaceuticals Inc., Edmonton (CA); Meiji Seika Pharma Co., Ltd., Tokyo (JP)

(72) Inventors: Michael Kammerer, Basel (CH); Frédéric Ran, Basel (CH)

(73) Assignees: FEDORA PHARMACEUTICALS INC., Edmonton (CA); MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 16/140,597

(22) Filed: Sep. 25, 2018

(65) Prior Publication Data
US 2019/0106421 A1    Apr. 11, 2019

Related U.S. Application Data

(60) Provisional application No. 62/563,803, filed on Sep. 27, 2017.

(51) Int. Cl.
| | | |
|---|---|---|
| A61K 31/439 | (2006.01) | |
| A61K 31/5377 | (2006.01) | |
| A61K 31/4985 | (2006.01) | |
| C07D 471/08 | (2006.01) | |
| A61K 31/551 | (2006.01) | |

(52) U.S. Cl.
CPC .......... C07D 471/08 (2013.01); A61K 31/551 (2013.01); *C07B 2200/13* (2013.01)

(58) Field of Classification Search
CPC .............. A61K 31/439; A61K 31/5377; A61K 31/4985; C07D 471/08
USPC ............... 514/300, 210.21, 211.15; 546/121
See application file for complete search history.

(56) References Cited

U.S. PATENT DOCUMENTS

| 8,796,257 B2 * | 8/2014 | Maiti | C07D 519/00 514/210.21 |
|---|---|---|---|
| 9,181,250 B2 | 11/2015 | Abe et al. | |
| 2015/0203503 A1 | 7/2015 | Patil et al. | |
| 2016/0272641 A1 | 9/2016 | Abe et al. | |

FOREIGN PATENT DOCUMENTS

| CN | 101264088 | 9/2008 |
|---|---|---|
| EP | 0 438 747 | 7/1991 |
| EP | 1 448 234 | 8/2004 |
| EP | 3 067 355 | 9/2016 |
| EP | 3 228 620 | 10/2017 |
| WO | 2015/046207 | 4/2015 |
| WO | 2015/053297 | 4/2015 |
| WO | 2016/088863 | 6/2016 |
| WO | 2016/116878 | 7/2016 |
| WO | 2016/120752 | 8/2016 |
| WO | 2016/151543 | 9/2016 |

OTHER PUBLICATIONS

International Search Report and Written Opinion, dated Jan. 30, 2019, of international application number PCT/IB2018/001185.
International Search Report and Written Opinion, dated Dec. 19, 2018, of international application No. PCT/IB2018/001187.
International Search Report and Written Opinion, dated Dec. 20, 2018, of international application No. PCT/IB2018/001204.
Baheti A. et al. "Excipients used in lyophilization of small molecules", J. Excipients Food Chem. 1(1):41-54 (2010).
Brittain H.G. et al. "Methods for the Characterization of Polymorphs", pp. 235 and 237 of Polymorphism in Pharmaceutical Solids, published by M. Dekker, New York, NY USA (1999).
Caira M.R. et al. "Crystalline Polymorphism of Organic Compounds" Topics in Current Chemistry 198:163-208 (1998).
Einfalt T. et al. "Methods of amorphization and investigation of the amorphous state" Acta Pharma. 63:305-334 (2013).
Kumar D.R. et al. "Formulation and Evaluation of Lyophilized Antibacterial Agent", Int. J. PharmTech Res. 5(4):1581-1589 (2013).
Morinaka et al., "OP0595, a new diazabicyclooctane: mode of action as a serine beta-lactamase inhibitor, antibiotic and beta-lactam 'enhancer'", J. Antimicrob. Chemo. 70:2779-2786 (2015).

* cited by examiner

*Primary Examiner* — Niloofar Rahmani
(74) *Attorney, Agent, or Firm* — Wenderoth, Lind & Ponack, L.L.P

(57) ABSTRACT

The present invention relates to a process for producing crystalline and amorphous forms of a diazabicyclooctane derivative represented by Compound (I) and methods for producing the same.

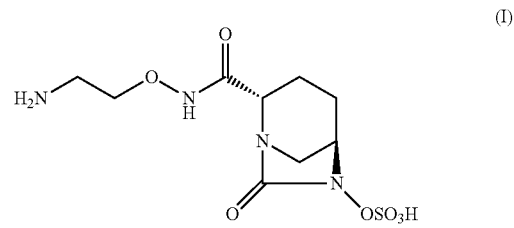

13 Claims, 1 Drawing Sheet

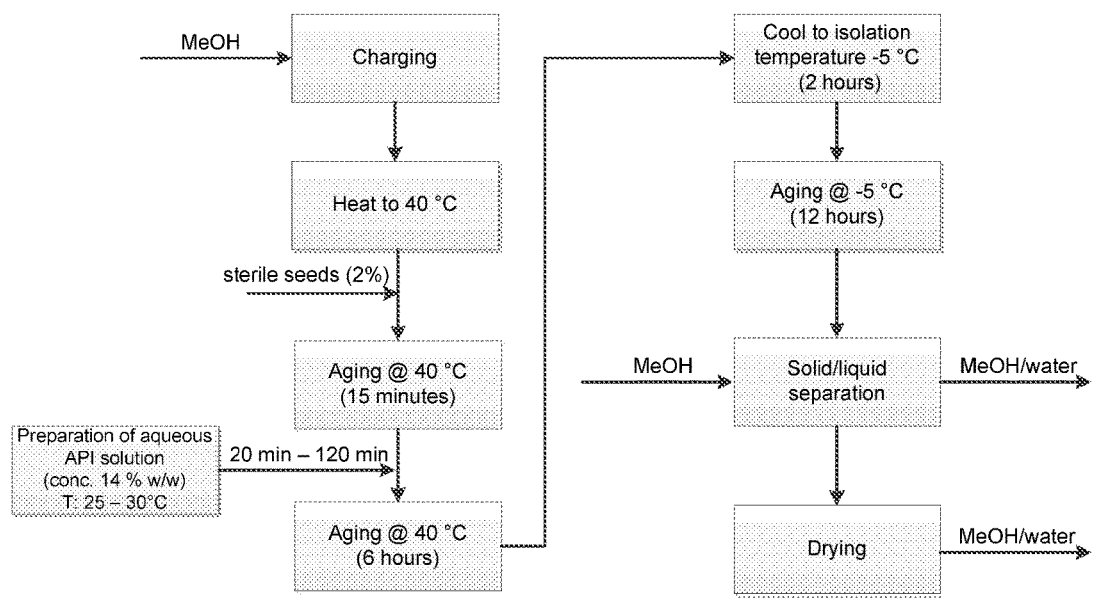

PHARMACEUTICAL FORMS OF DIAZABICYCLOOCTANE DERIVATIVES AND MANUFACTURING METHOD THEREOF

CROSS-REFERENCE TO RELATED APPLICATIONS

The present application claims the benefit of priority to U.S. Provisional Application No. 62/563,803 filed on Sep. 27, 2017, the entire contents of which is hereby incorporated by reference.

ACKNOWLEDGMENT OF GOVERNMENT SUPPORT

This invention was made with government support under Contract No. HHSO100201600038C awarded by the U.S. Department of Health and Human Services. The government has certain rights in the invention.

BACKGROUND

Penicillins and cephalosporins are β-lactam antibiotics that are widely and frequently used in the clinic. However, the acquisition of resistance to β-lactam antibiotics by various pathogens has had a damaging effect on maintaining the effective treatment of bacterial infections. The most significant known mechanism related to the acquisition of bacterial resistance is the production of class A, C, and D β-lactamases having a serine residue at the active center. These enzymes decompose the β-lactam antibiotic, resulting in the loss of the antimicrobial activities. Class A β-lactamases preferentially hydrolyze penicillins while class C β-lactamases have a substrate profile favoring cephalosporins.

Commercially available β-lactamase inhibitors, e.g., clavulanic acid, sulbactam, and tazobactam, are known and these inhibitors are effective mainly against class A β-lactamase producing bacteria, and used as a mixture with a penicillin antibiotic. However, 250 types or more of β-lactamases have been reported to date, including resistant bacteria which produce class A KPC-2 β-lactamase decomposing even carbapenem.

In recent years, infectious diseases caused by the above-mentioned resistant bacteria as pathogenic bacteria are found not only in severe infectious disease but also occasionally in community-acquired infectious disease. The currently available β-lactamase inhibitors are insufficient to inhibit the incessantly increasing β-lactamase and novel β-lactamase inhibitors which are required for the difficult treatment of bacterial infectious diseases caused by resistant bacteria. The development of antibacterial agents as well as β-lactamase inhibitors is in strong demand as the commercially available inhibitors become increasingly ineffective.

One of these antibacterial agents, (2S, 5R)—N-(2-aminoethoxy)-7-oxo-6-(sulfooxy)-1,6-diazabicyclo[3.2.1]octane-2-carboxamide, represented by Compound (I), is a "potent, broad-spectrum, non-β-lactam β-lactamase inhibitor" useful for antibiotic-resistant Gram-negative bacteria (Li, H.; Estabrook, M.; Jacoby, G. A.; Nichols, W. W.; Testa, R. T.; Bush, K. *Antimicrob Agents Chemother* 2015, 59, 1789-1793.) There are four crystalline forms of (2S, 5R)—N-(2-aminoethoxy)-7-oxo-6-(sulfooxy)-1,6-diazabicyclo[3.2.1]octane-2-carboxamide previously characterized and known in the art (see, e.g., International Publication no. WO 2015/053297).

While other crystalline forms have been previously characterized, large scale-up manufacturing processes which afford good reproducibility, high stability and high yield had not been achieved. When developing technologies for the commercial process, there are several factors and properties to consider when converting a small-scale lab process to a large manufacturing process suitable for clinical use.

One such factor includes solid state physical properties, for example, which entails the flowability of the milled solid, rate of dissolution and stability. The physical characteristics are influenced by the conformation and orientation of molecules in the unit cell, which defines a particular crystalline form of a substance. A crystalline form may give rise to thermal behavior different from that of the amorphous material or another crystalline form. Thermal behavior is measured in the laboratory using techniques such as capillary melting point, thermogravimetric analysis (TGA) and differential scanning calorimetry (DSC). These techniques may be used to distinguish between different crystalline forms. A particular crystalline form may show distinct spectroscopic properties that can be detected using powder X-ray diffractometry (XRPD), nuclear magnetic resonance (NMR) spectrometry, Raman spectroscopy and infrared (IR) spectrometry.

In deciding which crystalline form is preferable, the numerous properties of the crystalline forms must be compared and the preferred crystalline form chosen based on the many physical property variables in order to determine which properties afford a suitable manufacturing process which allows clinical use. In other processes, a particular crystalline form may be preferable in certain circumstances in which specific aspects, such as ease of preparation, stability, etc., are deemed to be critical. In other situations, a different crystalline form may be preferred for greater solubility and/or superior pharmacokinetics.

SUMMARY

The present application relates to a process for producing crystalline and amorphous forms of a diazabicyclooctane derivative represented by the following Compound (I):

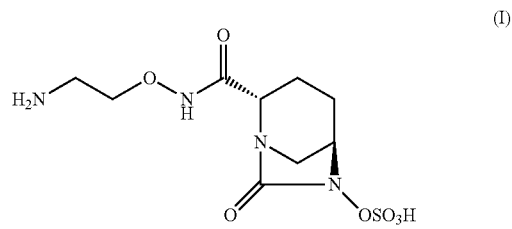

In an aspect of the invention, the present application provides a process for producing a crystalline Form IV of a Compound (I) comprising: (a) dissolving Compound (I) in water to form an aqueous solution of Compound (I); (b) adding the aqueous solution of Compound (I) to an alcohol to form a suspension; and (c) recovering the suspension to produce crystalline Form IV of Compound (I).

In an embodiment, the alcohol of step (b) is water-soluble. In an embodiment, the alcohol of step (b) is heated to a temperature of at least 30° C. or warmer. In an embodiment, the process further comprises adding seed crystals of Compound (I) to the alcohol. In another embodiment of the process, the aqueous solution of Compound (I) is added to the alcohol via sterile filtration.

In an embodiment, the suspension of step (c) is aged for at least 6 hours at a temperature of at least 25° C. or higher. In another embodiment, the heated suspension is cooled at −5° C. for at least 120 minutes. In an embodiment, the suspension is recovered via filtration, centrifugation, or evaporation. In an embodiment, the suspension is filtered or separated to form a filter-cake. In an embodiment, the filter-cake is rinsed with the same alcohol and then dried under reduced pressure at a temperature of 25° C. or higher.

In an embodiment, the process comprises recovering the suspension of step (c) via filtration or centrifugation. In an embodiment, crystalline Form IV is dried under reduced pressure.

In an embodiment, the crystalline Form IV of Compound (I) produced by the process is characterized by an X-ray power diffraction pattern having a characteristic peak expressed in values of degrees 2Θ at about 19.8±0.2. In another embodiment, the crystalline form is characterized by an X-ray power diffraction pattern having a characteristic peak expressed in values of degrees 2Θ at about 11.3±0.2. In an embodiment, the crystalline form is characterized by an X-ray power diffraction pattern having a characteristic peak expressed in values of degrees 2Θ at about 13.9±0.2.

In an embodiment, the crystalline Form IV of Compound (I) produced by the process is characterized by an X-ray power diffraction pattern having characteristic peaks expressed in values of degrees 2Θ at about 11.3; about 13.9, and about 19.8±0.2.

In another embodiment, the crystalline Form IV of Compound (I) produced by the process is characterized by an X-ray powder diffraction pattern having characteristic peaks expressed in values of degrees 2Θ at about 11.3; about 13.9, and about 19.8±0.2. In other embodiments, the crystalline form is characterized by an X-ray powder diffraction pattern having characteristic peaks expressed in values of degrees 2Θ at about 17.1; and about 22.2±0.2. In other embodiments, the crystalline form is characterized by an X-ray powder diffraction pattern having characteristic peaks expressed in values of degrees 2Θ at about 17.3 and about 22.7±0.2.

In an embodiment, the crystalline Form IV of Compound (I) is characterized by an X-ray powder diffraction pattern having characteristic peaks expressed in values of degrees 2Θ at about 11.3; about 13.9; about 17.1; about 19.8; about 22.2±0.2.

In an embodiment, the crystalline Form IV of Compound (I) is characterized by an X-ray powder diffraction pattern having characteristic peaks expressed in values of degrees 2Θ at about 11.3; about 13.9; about 17.1; about 17.3; about 19.1; about 19.8; about 22.2; about 22.7; about 23.4; about 23.8; about 24.1; about 24.6; about 26.5; about 27.7 and about 28.0±0.2.

In an aspect of the invention, the present application provides a pharmaceutical composition comprising crystalline Form IV of Compound (I) produced via the processes described herein and a pharmaceutically acceptable carrier, pharmaceutical excipient, or a pharmaceutical diluent.

In an aspect of the invention, the present application provides a process for producing an amorphous form of a compound represented by Compound (I) comprising: dissolving Compound (I) in water to form an aqueous solution of Compound (I); and (b) evaporating the aqueous solution at reduced pressure at a temperature greater than room temperature to produce the amorphous form of Compound (I). In an embodiment, the process comprises evaporating the aqueous solution at a temperature greater than at least 45° C. In another embodiment, the process comprises evaporating the aqueous solution at a temperature greater than at least 60° C. In an embodiment, the process comprises evaporating the aqueous solution a reduced pressure of about 30 mbar. In another embodiment, the process for producing an amorphous form of a compound represented by Compound (I) is accomplished without the use of a stabilizer.

In another aspect, the present application provides a pharmaceutical composition comprising an amorphous form of Compound (I) disclosed herein and a pharmaceutically acceptable carrier, pharmaceutical excipient, or a pharmaceutical diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE FIGURE

The following detailed description, given by way of example, but not intended to limit the invention solely to the specific embodiments described, may best be understood in conjunction with the accompanying FIGURE.

FIG. 1 illustrates a general procedure for using methanol as the anti-solvent to produce crystalline Form IV.

DETAILED DESCRIPTION

In the following description, certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, and unless noted to the contrary, the following terms and phrases have the meaning noted below.

The crystalline and amorphous forms of Compound (I) can exist in various isomeric forms, as well as in one or more tautomeric forms, including both single tautomers and mixtures of tautomers. The term "isomer" is intended to encompass all isomeric forms of a compound of this invention, including tautomeric forms of the compound. The term "tautomer" refers to a proton shift from one atom of a molecule to another atom of the same molecule.

Compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The present invention contemplates various stereoisomers and mixtures thereof and includes "enantiomers", which refers to two stereoisomers whose molecules are nonsuperimposeable mirror images of one another.

If there is a discrepancy between a depicted structure and a name given to that structure, then the depicted structure controls. Throughout the present application, Compound (I) is used interchangeable with (2S, 5R)—N-(2-aminoethoxy)-7-oxo-6-(sulfooxy)-1,6-diazabicyclo[3.2.1]octane-2-carboxamide. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The crystalline and amorphous forms of Compound (I) may be isotopically-labelled by having one or more atoms replaced by an atom having a different atomic mass or mass number. Examples of isotopes that can be incorporated into Compound (I) include isotopes of hydrogen, carbon, nitrogen, oxygen, phosphorous, fluorine, chlorine, or iodine. Illustrative of such isotopes are $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds can be used to measure the biodistribution, tissue concentration and the kinetics of transport and excretion from biological tissues including a subject to which such a labelled compound is administered. Labeled compounds are also used to determine therapeutic effectiveness, the site or mode of action, and the binding affinity of a candidate therapeutic to a pharmacologically important target. Certain radioactive-labelled crystalline and amorphous forms of Compound (I), therefore, are useful in drug and/or tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron emitting isotopes, such as $^{11}$C, $^{18}$F, $^{15}$O and $^{13}$N, provides labeled analogs of the inventive compounds that are useful in Positron Emission Tomography (PET) studies, e.g., for examining substrate receptor occupancy. Isotopically-labeled Compound (I) can generally be prepared by conventional techniques known to those skilled in the art or by processes analogous to those described in the Preparations and Examples section as set out below using an appropriate isotopic-labeling reagent.

Embodiments of the invention disclosed herein are also meant to encompass the in vivo metabolic products of Compound (I). Such products may result from, for example, the oxidation, reduction, hydrolysis, amidation, esterification, dimerization and like processes primarily due to enzymatic activity upon administration of a compound of the invention. Accordingly, the invention includes compounds that are produced as by-products of enzymatic or non-enzymatic activity on an inventive compound following the administration of such a compound to a mammal for a period of time sufficient to yield a metabolic product. Metabolic products, particularly pharmaceutically active metabolites are typically identified by administering a radiolabelled compound of the invention in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabelled compound.

The invention also provides pharmaceutically acceptable salt forms of crystalline and amorphous forms of Compound (I). Encompassed within the scope of the invention are both acid and base addition salts that are formed by contacting a pharmaceutically suitable acid or a pharmaceutically suitable base with crystalline and amorphous forms of the invention.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases, the compounds of the invention may merely retain adventitious water or be a mixture of water plus some adventitious solvent.

In some embodiments, the experimental powder diffraction patterns were recorded at ambient conditions in transmission geometry with a Stoe Stadi P diffractometer (Cu Kα1 radiation [1.5406 Å], 40 kV and 40 mA, primary beam monochromator, silicon strip detector, angular range 3° to 42° 2Theta with a step size of 0.02° 2Theta, approximately 30 minutes total measurement time). The samples were prepared and analyzed without further processing (e.g. grinding or sieving) of the substance.

In some embodiments, the single crystal X-ray intensity data were collected at 100(2) K using a Gemini R Ultra diffractometer (Rigaku) with Cu—K-alpha-radiation (1.54184 Å) and processed with the Crysalis-package. Structure solution and refinement was performed using the ShelXTL software (Bruker AXS, Karlsruhe).

One skilled in the art will understand that the relative intensities and positions of the peaks obtained by X-ray powder diffraction may vary depending upon factors such as, the sample preparation technique, the sample mounting procedure and the particular instrument employed. For example, in additional embodiments, the listed X-ray powder diffraction pattern peaks for the crystalline form of Compound (I) may be about ±0.2 degrees 2Θ.

It is known that an X-ray powder diffraction pattern may be obtained which has one or more measurement errors depending on measurement conditions (such as equipment or machine used). Intensities in an X-ray powder diffraction pattern may fluctuate depending on measurement conditions. Therefore, it should be understood that the crystalline forms of the present invention are not limited to the crystals that provide X-ray powder diffraction patterns identical to the X-ray powder diffraction patterns described in this application, and any crystals providing X-ray powder diffraction patterns substantially the same as those described in the application fall within the scope of the present invention. For example, relative intensity of peaks can be affected by grains above 30 microns in size and non-unitary aspect ratios, which may affect analysis of samples. A person skilled in the art will recognize that the position of reflections can be affected by the precise height at which the sample sits in the diffractometer and the zero calibration of the diffractometer. The surface planarity of the sample may also have a small effect. Therefore, the diffraction pattern data described herein are not to be taken as absolute values. (Jenkins, R & Snyder, R. L. "Introduction to X-Ray Powder Diffractometry" John Wiley & Sons 1996; Bunn, C. W.

(1948), Chemical Crystallography, Clarendon Press, London; Klug, H. P. & Alexander, L. E. (1974), X-Ray Diffraction Procedures).

Generally, a measurement error of plus or minus 0.2° 2Θ, and such degree of a measurement error should be taken into account when considering the X-ray powder diffraction patterns described in this application. Furthermore, it should be understood that intensities may fluctuate depending on experimental conditions and sample preparation (preferred orientation).

In one aspect, substantially pure crystalline and amorphous forms of the present invention are provided. For example, the present invention includes a crystalline Form IV of Compound (I) as described in this application that is about ≥95% pure. For example, the forms may be about ≥95%, ≥96%, ≥97%, ≥98% or ≥99% pure.

In some embodiments, the crystalline Form IV or amorphous form of Compound (I) is isolated in a substantially pure form. The forms described herein may have purity of more than about 90%, about 91%, about 92%, about 93%, about 94%, about 95%, about 96%, about 97%, about 98%, or about 99% by weight. In a further embodiment, the forms may have a purity of more than about 95% by weight. For example, the forms may be ≥95%, ≥96%, ≥97%, ≥98% or ≥99% pure.

The inventive crystalline or amorphous forms are synthesized using conventional synthetic methods, and more specifically using the general methods noted below. Specific synthetic protocols for several compounds in accordance with the present invention are described in the Examples.

EXAMPLES

According to the series of production processes of the present invention, crystalline forms of the aforementioned Compound (I), particularly crystalline Form IV, can be produced with good reproducibility, high stability and high yield. Further, crystalline Form IV provides favorable storage stability, allows for sterile filtration, and allows storage at higher temperatures (e.g., safety temperature of 100° C.). When converting the small-scale lab process to a large manufacturing process, it was discovered that the processes described herein allowed for sterile filtration, a requirement of the manufacturing process to make it suitable for clinical use. Table 1 provides the XRPD pattern of the crystalline Form IV of Compound (I) produced on a large-scale suitable for clinical use, e.g., manufacturing scale, wherein the process allows for sterile filtration. Table 2 provides the single crystal structural data for Form IV of Compound (I).

The following examples are provided for purpose of illustration and not limitation. General Reaction Scheme for the formation of Crystalline Form IV:

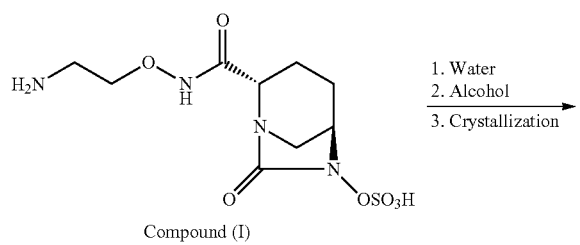

Compound (I)

1. Water
2. Alcohol
3. Crystallization

-continued

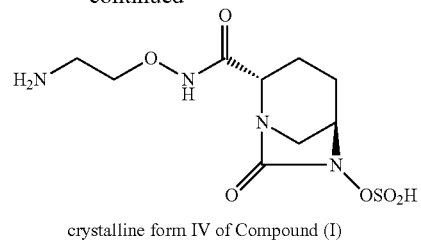

crystalline form IV of Compound (I)

The crystalline Form IV of (2S, 5R)—N-(2-aminoethoxy)-7-oxo-6-(sulfooxy)-1,6-diazabicyclo[3.2.1]octane-2-carboxamide was prepared through several steps as illustrated in the general reaction scheme above. In one vessel, Compound (I) was dissolved in heated water (at least above room temperature). In a second vessel, a water-soluble alcohol was heated. In an optional step, seed crystals of Compound (I) were added to the heated alcohol and allowed to age for 15 minutes.

The aqueous solution of Compound (I) of the first vessel was added via filter to the alcoholic phase of the second vessel at about 40° C. within about 20 minutes and formed a suspension. The suspension was aged for about 6 hours at 40° C. The suspension was then cooled to −5° C. for at least 120 minutes. The cooled suspension was optionally aged for 12 hours and then filtered or separated via centrifugation. The filtered product, i.e., the filter-cake, was rinsed with the anti-solvent alcohol and dried at 40° C. under reduced pressure overnight.

General Procedure for Methanol as Anti-Solvent (See FIG. 1)

A 5-L glass reactor was charged with a mixture of heated water (25°-30° C.) and Compound (I) for 30 minutes. In a separate crystallization reactor, methanol was heated to 40° C. Subsequently, 2% (w/w) Compound (I), crystalline Form IV seed crystals were added to the solution and the solution was aged for 15 minutes. The aqueous solution of Compound (I) was added via a sterile filter to the seeded and aged methanolic phase at 40° C. within 20 minutes. At the end of addition, the solvent ratio water/methanol amounted to 25:75 (w/w). The suspension was then aged for 6 hours at 40° C. The suspension was cooled to −5° C. within 120 minutes, aged for 12 hours and then filtered. The filter-cake was rinsed with methanol and dried at 40° C. in vacuo (10 mbar) overnight to afford a white solid in 91% yield.

General Procedure for Ethanol as Anti-Solvent

A glass reactor was charged with a mixture of heated water (25°-30° C.) and Compound (I) for 30 minutes. In a separate and parallel process, ethanol was added via sterile filter at ambient temperature in a crystallization reactor. Subsequently, 10% of the above prepared aqueous solution of Compound (I) was added via sterile filter to the ethanol phase and aged for 15 minutes. During addition, spontaneous nucleation occurred. The suspension was further aged under stirring for 30 minutes. Afterwards, the remaining 90% of the above prepared aqueous solution of Compound (I) was added via a sterile filter at ambient temperature within 60 minutes to the seeded ethanol phase. After addition, the resulting suspension was cooled to −5° C. within 60 minutes and aged at this temperature for approximately 4 to 15 hours. The crystals were isolated via filtration and rinsed with cold ethanol (−5° C.) which yielded a wet solid. The wet solid was dried over night at 25° C. at reduced pressure (50-100 mbar) to afford the desired crystalline form in 84.2% corrected yield as white powder.

TABLE 1

Powder X-ray diffraction of crystalline Form IV
Powder X-ray diffraction of Form IV

| Degree 2-theta | Relative intensity (%) |
|---|---|
| 11.3 | 52 |
| 13.9 | 59 |
| 17.1 | 40 |
| 17.3 | 16 |
| 19.1 | 21 |
| 19.8 | 100 |
| 22.2 | 30 |
| 22.7 | 12 |
| 23.4 | 16 |
| 23.8 | 16 |
| 24.1 | 19 |
| 24.6 | 17 |
| 26.5 | 16 |
| 27.7 | 15 |
| 28.0 | 11 |

TABLE 2

Single crystal structural data of Form IV

| Crystalline form | Form IV |
|---|---|
| Solid form description | Polymorph |
| Measuring Temperature | 100 (2) K |
| Crystal system | Orthorhombic |
| Space group | P2(1)2(1)2(1) |
| Unit cell dimensions | |
| a = | 10.500 (2) Å |
| b = | 10.823 (2) Å |
| c = | 11.639 (2) Å |
| α = | 90° |
| β = | 90° |
| γ = | 90° |
| Cell volume | 1322.7 (5) Å$^3$ |
| API molecules in unit cell | 4 |
| Calculated density | 1.629 g/cm$^3$ |

General Procedure for Preparation of Amorphous Material by Fast Evaporation

A round-bottom flask was charged with 200 mg of Compound (I) and 5.0 mL of water (HPLC grade) at 22° C. The obtained mixture was agitated until complete dissolution. The clear solution was concentrated via rotary evaporation at 65° C. at reduced pressure (30 mbar). Fast evaporation afforded a white precipitate material.

The various embodiments described above can be combined to provide further embodiments. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A process for producing a crystalline Form IV of a compound represented by:

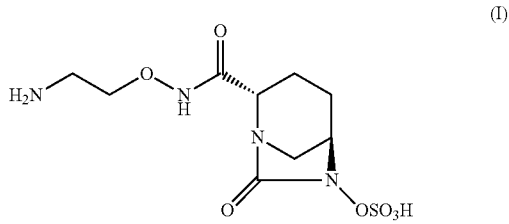

(I)

comprising:
(a) dissolving Compound (I) in water to form an aqueous solution of Compound (I);
(b) adding the aqueous solution of Compound (I) to an alcohol to form a suspension; and
(c) recovering the suspension to produce crystalline Form IV of Compound (I)
wherein the crystalline Form IV is characterized by an X-ray powder diffraction pattern having characteristic peaks expressed in values of degrees 2Θ at about 17.1; about 19.1; about 22.2; about 23.4; about 23.8; about 24.1; about 24.6; about 26.5; about 27.7; and about 28.0±0.2.

2. The process according to claim 1, wherein the alcohol is water-soluble.

3. The process according to claim 1, wherein the alcohol is heated to a temperature of at least 30° C. or warmer.

4. The process according to claim 1, wherein seed crystals of Compound (I) are added to the alcohol.

5. The process according to claim 1, wherein the aqueous solution of Compound (I) is added to the alcohol via sterile filtration.

6. The process according to claim 1, wherein the suspension is aged for at least 6 hours at a temperature of at least 25° C. or higher.

7. The process according to claim 6, wherein the heated suspension is cooled at −5° C. for at least 120 minutes.

8. The process according to claim 1, wherein the suspension is recovered via filtration, centrifugation or evaporation.

9. The process according to claim 1, wherein the suspension is filtered or separated to form a filter-cake.

10. The process according to claim 9, wherein the filter-cake is rinsed with the same alcohol and then dried under reduced pressure at a temperature of 25° C. or higher.

11. The process according to claim 1, wherein the suspension is recovered via filtration or centrifugation.

12. The process according to claim 1, wherein crystalline Form IV is dried under reduced pressure.

13. The process according to claim 1, wherein the crystalline Form IV is characterized by an X-ray powder diffraction pattern having characteristic peaks expressed in values of degrees 2Θ at about 11.3; about 13.9; about 17.1; about 17.3; about 19.1; about 19.8; about 22.2; about 22.7; about 23.4; about 23.8; about 24.1; about 24.6; about 26.5; about 27.7; and about 28.0±0.2.

* * * * *